United States Patent
Ou et al.

(10) Patent No.: US 9,783,460 B2
(45) Date of Patent: *Oct. 10, 2017

(54) PROCESS FOR CONVERTING OXYGENATES TO AROMATIC HYDROCARBONS

(71) Applicant: ExxonMobil Chemical Patents Inc., Baytown, TX (US)

(72) Inventors: John D. Ou, Houston, TX (US); Machteld M. Mertens, Flemington, NJ (US); Linelle T. Jacob, Humble, TX (US); Stephen J. McCarthy, Center Valley, PA (US); Rohit Vijay, Bridgewater, NJ (US); Jeevan S. Abichandani, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 189 days.

This patent is subject to a terminal disclaimer.

(21) Appl. No.: 14/560,850

(22) Filed: Dec. 4, 2014

(65) Prior Publication Data

US 2015/0175498 A1 Jun. 25, 2015

Related U.S. Application Data

(60) Provisional application No. 62/003,290, filed on May 27, 2014, provisional application No. 61/918,984, (Continued)

(30) Foreign Application Priority Data

Jul. 7, 2014 (EP) .................................... 14176022

(51) Int. Cl.
*C07C 1/24* (2006.01)
*C07C 7/00* (2006.01)
(Continued)

(52) U.S. Cl.
CPC .................. *C07C 1/22* (2013.01); *C07C 1/24* (2013.01); *C07C 2/64* (2013.01); *C07C 5/2729* (2013.01);
(Continued)

(58) Field of Classification Search
None
See application file for complete search history.

(56) References Cited

U.S. PATENT DOCUMENTS 3,354,078 A 11/1967 Maile et al.
3,702,886 A 11/1972 Argauer et al.
(Continued)

FOREIGN PATENT DOCUMENTS

CN 101602643 12/2009
CN 101602648 12/2009
(Continued)

OTHER PUBLICATIONS

U.S. Appl. No. 14/560,889, filed Dec. 4, 2014, Ou et al.
(Continued)

*Primary Examiner* — Philip Louie (57) ABSTRACT

Embodiments of the invention provide processes for catalytically converting oxygenates to hydrocarbon products having an increased $C_6$-$C_8$ aromatics content therein. Particular processes include (a) providing a first mixture comprising ≥10.0 wt. % of at least one oxygenate, based on the weight of the first mixture; (b) contacting the first mixture with a catalyst to convert the first mixture to a product stream including water, one or more hydrocarbons, hydrogen, and one or more oxygenates, wherein the catalyst comprises at least one molecular sieve and at least one element selected from Groups 2-14 of the Periodic Table and the hydrocarbons comprise ≥30.0 wt. % of aromatics, based on the weight of the hydrocarbons in the product stream; and (c) separating from the product stream at least one water-rich stream, at least one aromatic-rich hydrocarbon stream, and at least one aromatic-depleted hydrocarbon stream.

26 Claims, 3 Drawing Sheets

Related U.S. Application Data filed on Dec. 20, 2013, provisional application No. 61/918,994, filed on Dec. 20, 2013, provisional application No. 61/919,013, filed on Dec. 20, 2013.

(51) Int. Cl.

| | | |
|---|---|---|
| C07C 1/20 | (2006.01) | |
| C07C 1/22 | (2006.01) | |
| C07C 2/64 | (2006.01) | |
| C07C 5/27 | (2006.01) | |
| C07C 6/06 | (2006.01) | |
| C07C 6/00 | (2006.01) | |
| C10G 3/00 | (2006.01) | |
| C10G 29/20 | (2006.01) | |

(52) U.S. Cl.
CPC .............. *C07C 6/00* (2013.01); *C07C 6/06* (2013.01); *C10G 3/49* (2013.01); *C10G 29/205* (2013.01); *C07C 2529/40* (2013.01); *C10G 2400/30* (2013.01); *Y02P 30/20* (2015.11); *Y02P 30/42* (2015.11)

(56) References Cited

U.S. PATENT DOCUMENTS

| | | |
|---|---|---|
| 3,709,979 A | 1/1973 | Chu |
| 3,760,024 A | 9/1973 | Cattanach |
| 3,832,449 A | 8/1974 | Rosinski et al. |
| 3,894,102 A | 7/1975 | Chang et al. |
| 3,894,103 A | 7/1975 | Chang et al. |
| 3,894,104 A | 7/1975 | Chang et al. |
| 3,894,107 A | 7/1975 | Butter et al. |
| 3,928,483 A | 12/1975 | Chang et al. |
| 3,960,978 A | 6/1976 | Givens et al. |
| 3,969,426 A * | 7/1976 | Owen ................ C07C 1/20 585/14 |
| 4,016,218 A | 4/1977 | Haag et al. |
| 4,016,245 A | 4/1977 | Plank et al. |
| 4,021,502 A | 5/1977 | Plank et al. |
| 4,025,571 A | 5/1977 | Lago |
| 4,035,430 A | 7/1977 | Dwyer et al. |
| 4,046,685 A | 9/1977 | Bray |
| 4,049,573 A | 9/1977 | Kaeding |
| 4,058,576 A | 11/1977 | Chang et al. |
| 4,076,842 A | 2/1978 | Plank et al. |
| 4,079,095 A | 3/1978 | Givens et al. |
| 4,088,706 A | 5/1978 | Kaeding |
| RE29,948 E | 3/1979 | Dwyer et al. |
| 4,150,062 A | 4/1979 | Garwood et al. |
| 4,157,293 A | 6/1979 | Plank et al. |
| 4,211,640 A | 7/1980 | Garwood et al. |
| 4,227,992 A | 10/1980 | Garwood et al. |
| 4,288,645 A | 9/1981 | Wagstaff |
| 4,291,182 A | 9/1981 | Dautzenberg et al. |
| 4,326,994 A | 4/1982 | Haag et al. |
| 4,397,827 A | 8/1983 | Chu |
| 4,403,044 A | 9/1983 | Post et al. |
| 4,417,780 A | 11/1983 | Knapp |
| 4,423,274 A | 12/1983 | Daviduk et al. |
| 4,433,185 A | 2/1984 | Tabak |
| 4,433,189 A | 2/1984 | Young |
| 4,450,311 A | 5/1984 | Wright et al. |
| 4,456,779 A | 6/1984 | Owen et al. |
| 4,538,017 A | 8/1985 | Butler et al. |
| 4,556,477 A | 12/1985 | Dwyer |
| 4,579,993 A | 4/1986 | Bowes et al. |
| 4,582,815 A | 4/1986 | Bowes |
| 4,584,423 A | 4/1986 | Nacamuli et al. |
| 4,590,321 A | 5/1986 | Chu |
| 4,621,161 A | 11/1986 | Shihabi |
| 4,628,135 A | 12/1986 | Owen et al. |
| 4,665,251 A | 5/1987 | Chu |
| 4,720,602 A | 1/1988 | Chu |
| 4,788,369 A | 11/1988 | Marsh et al. |
| 4,808,763 A | 2/1989 | Shum |
| 5,365,004 A | 11/1994 | Beck et al. |
| 5,367,099 A | 11/1994 | Beck et al. |
| 5,625,103 A | 4/1997 | Abichandani et al. |
| 5,633,417 A | 5/1997 | Beck et al. |
| 5,675,047 A | 10/1997 | Beck et al. |
| 5,705,726 A | 1/1998 | Abichandani et al. |
| 5,877,368 A | 3/1999 | Kiyama et al. |
| 5,883,034 A | 3/1999 | Drake et al. |
| 5,998,688 A | 12/1999 | Abichandani et al. |
| 6,028,238 A | 2/2000 | Beck et al. |
| 6,048,815 A | 4/2000 | Yao et al. |
| 6,156,689 A | 12/2000 | Kimble et al. |
| 6,177,374 B1 | 1/2001 | Pradhan et al. |
| 6,187,982 B1 | 2/2001 | Beck et al. |
| 6,372,680 B1 | 4/2002 | Wu et al. |
| 6,372,949 B1 | 4/2002 | Brown et al. |
| 6,417,421 B1 | 7/2002 | Yao |
| 6,423,879 B1 | 7/2002 | Brown et al. |
| 6,504,072 B1 | 1/2003 | Brown et al. |
| 6,506,954 B1 * | 1/2003 | Brown ................ C07C 1/20 585/469 |
| 7,285,511 B2 | 10/2007 | Ghosh et al. |
| 7,304,194 B2 | 12/2007 | Ghosh et al. |
| 7,453,018 B2 | 11/2008 | Dakka et al. |
| 7,722,825 B1 | 5/2010 | Bozzano et al. |
| 7,799,962 B2 | 9/2010 | Dakka et al. |
| 2006/0161035 A1 | 7/2006 | Kalnes et al. |
| 2009/0124841 A1 * | 5/2009 | Rothaemel ............ B01D 3/143 585/639 |
| 2013/0123557 A1 | 5/2013 | McCarthy et al. |
| 2013/0158323 A1 | 6/2013 | Mondal |
| 2013/0165725 A1 | 6/2013 | Chewter et al. |
| 2013/0281753 A1 | 10/2013 | McCarthy et al. |
| 2013/0303814 A1 | 11/2013 | Mammadov et al. |
| 2014/0018592 A1 | 1/2014 | Chen et al. |

FOREIGN PATENT DOCUMENTS

| | | |
|---|---|---|
| CN | 101607864 | 12/2009 |
| CN | 101780417 | 7/2010 |
| CN | 101823929 | 9/2010 |
| EP | 0 123 449 | 10/1984 |
| EP | 0 172 686 | 2/1986 |
| WO | WO 99/51549 | 10/1999 |
| WO | WO 01/29152 | 4/2001 |
| WO | WO 2005/068406 | 7/2005 |
| WO | WO 2006/012150 | 2/2006 |
| WO | WO 2009/021726 | 2/2009 |
| WO | WO 2013/017497 | 2/2013 |

OTHER PUBLICATIONS

U.S. Appl. No. 62/003,290, filed May 27, 2014, Ou et al.
U.S. Appl. No. 61/918,984, filed Dec. 20, 2013, McCarthy et al.
U.S. Appl. No. 61/918,994, filed Dec. 20, 2013, McCarthy et al.
U.S. Appl. No. 61/919,013, filed Dec. 20, 2013, McCarthy et al.
U.S. Appl. No. 62/057,855, filed Sep. 30, 2014, Buchanan et al.
Chang et al., "The Conversion of Methanol and Other O-Compounds to Hydrocarbons over Zeolite Catalysts," Journal of Catalysis, vol. 47 (1977), pp. 249-259.
Ono et al., "Selective Conversion of Methanol into Aromatic Hydrocarbons over Zinc-exchanged ZSM-5 Zeolites," Journal of the Chemical Society, Faraday Transactions 1, vol. 84, No. 4, Jan. 1988, p. 1091-1099.
Inoue et al., "Selective conversion of methanol into aromatic hydrocarbons over silver-exchanged ZSM-5 zeolites," Microporous Materials, vol. 4, No. 5, Aug. 1995, pp. 379-383.
Woltermann et al., "Chapter 4 Commercial Preparation and Characterization of FCC Catalysts", Studies in Surface Science and Catalysis, 1993, vol. 76, pp. 105-144.
Eastwood et al., "Thermofor Catalytic Cracking Unit", Industrial and Engineering Chemistry, Dec. 1947, vol. 39, No. 12, pp. 1685-1690.

* cited by examiner

PROCESS FOR CONVERTING OXYGENATES TO AROMATIC HYDROCARBONS

CROSS REFERENCE TO RELATED APPLICATIONS

This application claims priority to Provisional U.S. Patent Application Ser. No. 62/003,290, filed May 27, 2014; Provisional U.S. Patent Application Ser. No. 61/918,984 filed Dec. 20, 2013; Provisional U.S. Patent Application Ser. No. 61/918,994 filed Dec. 20, 2013; Provisional U.S. Patent Application Ser. No. 61/919,013 filed Dec. 20, 2013; and EP 14176022.3 filed Jul. 7, 2014, the disclosures of which are incorporated herein by reference in their entireties.

FIELD OF THE INVENTION

Embodiments of the invention relate to processes for converting oxygenates to aromatic hydrocarbons. In particular, embodiments of the invention related to the conversion of methanol to $C_6$-$C_8$ aromatic hydrocarbons.

BACKGROUND OF THE INVENTION

Aromatic hydrocarbons, such as benzene, toluene, xylene, etc. are useful as fuels, solvents, and as feeds for various chemical processes. Of the aromatics, those having 6 to 8 carbon atoms (e.g., benzene, toluene, and xylene) are especially desired. Para-xylene ("p-xylene") is particularly useful for manufacturing phthalic acids such as terephthalic acid, which is an intermediate in the manufacture of synthetic fibers such as polyester fibers.

One conventional process for producing aromatics involves reacting an oxygenate, such as methanol, in the presence of zeolite, such as ZSM-5, to produce water and a hydrocarbon product containing aromatics. See, e.g., C. D. Chang and A. J. Silvestri, Journal of Catalysis 47, p. 249 (1977), which discloses a process featuring high methanol conversion in approximately stoichiometric yield to produce about 44 wt. % hydrocarbon and about 56 wt. % of water, based on total product weight. Water and a portion of the hydrocarbon are condensed by exposing the product to a temperature <100° C., with the vapor being recycled to the reactor inlet. The vapor, which comprises about 20 wt. % of the hydrocarbon product, contains primarily $C_1$-$C_4$ paraffin and $C_2$-$C_4$ olefin. At a reaction temperature of about 370° C. and a liquid hourly space velocity (LHSV) of approximately 1.0 hr$^{-1}$, approximately 80 wt. % of the hydrocarbon product comprises gasoline boiling-range hydrocarbons, including $C_6$-$C_{11}$ aromatics. Under these conditions, the hydrocarbon product comprises approximately 30 wt. % of $C_6$-$C_8$ aromatics and approximately 10 wt. % of $C_{9+}$ hydrocarbon, primarily 1,2,4,5-tetramethylbenzene (i.e., durene). Durene can be removed by selectively hydrotreating the aromatic portion of the hydrocarbon product.

It is desired to convert oxygenates to hydrocarbons with an increase in the relative amount of $C_6$-$C_8$ aromatics in the hydrocarbon product as the $C_6$-$C_8$ aromatics are commercially useful. It is particularly desired to do so without increasing (i) the relative amount of durene in the aromatic portion of the hydrocarbon product to avoid extensively treating the product to remove durene toxic and/or (ii) the rate of catalyst deactivation. It is even more desired to do this while increasing the relative amount of p-xylene in the hydrocarbon product since p-xylene is the most commercially desired of the $C_6$-$C_8$ aromatics.

SUMMARY OF THE INVENTION

It has been found that oxygenates can be catalytically converted to hydrocarbon products having an increased $C_6$-$C_8$ aromatics content in the hydrocarbon product compared to conventional processes. The process utilizes a catalyst comprising (i) ≥10.0 wt. % of at least one molecular sieve and (ii) ≥0.1 wt. % of at least one element selected from Groups 2-14 of the Periodic Table. The invention is based in part on the discovery that utilizing one or more elements from Groups 2-14 of the Periodic Table provides the catalyst with a dehydrogenation functionality that surprisingly produces molecular hydrogen and an increased aromatics yield, but without producing a significant amount of carbon monoxide.

It has also been found that recycling and combining at least a portion of the aromatics in the hydrocarbon product with the oxygenate unexpectedly leads to one or more of the following advantages. In particular embodiments, recycling and combining at least a portion of the aromatics in the hydrocarbon product provides an increase in the relative amount of aromatics in the hydrocarbon product. The increase in aromatics may be achieved without a significant increase in the rate of catalyst deactivation and/or without a significant increase in the relative amount of durene in the aromatic portion of the hydrocarbon product. Advantageously and contrary to expectations, recycling and combining with the oxygenate at least a portion of the aromatics in the hydrocarbon product does not suppress methanol conversion to aromatic products. Under particular conditions, recycling of the aromatics can actually provide an overall increase in product aromatics content. Surprisingly, the catalyst may not experience a significant increase in deactivation rate, e.g., from over-reacting the recycled aromatics, even at elevated reaction temperatures (e.g., end of run conditions). And under certain conditions, the relative amount of durene in the aromatic portion of the product may not increase, even though recycling of xylenes to a chemical environment rich in $CH_2$ fragments would be expected to result in alkylation to $C_{9+}$ aromatics. At least a portion of the olefins and paraffins in the hydrocarbon product may be recycled as well, leading to further conversion of the olefins and paraffins to aromatics without causing a significant increase in catalyst deactivation.

The process can be operated continuously, semi-continuously, or even in batch mode. The catalyst can be located within a reactor, e.g., in one or more fixed beds. More than one reactor can be utilized, the reactors being arranged, e.g., in series, parallel, or series-parallel.

DETAILED DESCRIPTION

The present process is useful for the conversion a first mixture comprising oxygen-containing organic compounds (i.e., "oxygenates") into hydrocarbon products where the conversion is carried out by an exothermic catalytic reaction.

As used herein the phrase "at least a portion of" means 1.0 to 100.0 wt. % of the process stream or composition to which the phrase refers. The upper limit on the range to which the phrase "at least a portion of" refers, may be 1.0 wt. %, 2.0 wt. %, 5.0 wt. %, 10.0 wt. %, 20.0 wt. %, 25.0 wt. %, 30.0 wt. %, 40.0 wt. %, 50.0 wt. %, 60.0 wt. %, 70.0 wt. %, 75.0 wt. %, 80.0 wt. %, 90.0 wt. %, 95.0 wt. %, 98.0 wt. %, 99.0 wt. %, or 100.0 wt. %. The lower limit on the range to which the phrase "at least a portion of" refers may be selected from 1.0 wt. %, 2.0 wt. %, 5.0 wt. %, 10.0 wt. %, 20.0 wt. %, 25.0 wt. %, 30.0 wt. %, 40.0 wt. %, 50.0 wt. %, 60.0 wt. %, 70.0 wt. %, 75.0 wt. %, 80.0 wt. %, 90.0 wt. %, 95.0 wt. %, 98.0 wt. %, 99.0 wt. %, or 100.0 wt. %. Ranges expressly disclosed include combinations of any of the above-enumerated upper and lower limits; e.g., 10.0 to 100.0 wt. %, 10.0 to 98.0 wt. %, 2.0 to 10.0, 40.0 to 60.0 wt. %, etc.

The initial feedstream or "first mixture" used herein is a hydrocarbon-containing composition including one or more oxygenates. Typically, the first mixture comprises ≥10.0 wt. % of at least one oxygenate, based on the weight of the first mixture. The upper limit on the amount of oxygenate(s) in the first mixture may be 10.0 wt. %, 12.5 wt. %, 15.0 wt. %, 20.0 wt. %, 25.0 wt. %, 30.0 wt., 35.0 wt. % 40.0 wt. %, 45.0 wt. %, 50.0 wt. %, 55.0 wt. %, 60.0 wt. %, 65.0 wt. %, 70.0 wt. %, 75.0 wt. %, 80.0 wt. %, 85.0 wt. %, 90.0 wt. %, 95.0 wt. %, 99.0 wt. %, 99.5 wt. %, or 100.0 wt. %. The lower limit on the amount of oxygenate in the first mixture may be 10.0 wt. %, 12.5 wt. %, 15.0 wt. %, 20.0 wt. %, 25.0 wt. %, 30.0 wt. %, 35.0 wt. % 40.0 wt. %, 45.0 wt. %, 50.0 wt. %, 55.0 wt. %, 60.0 wt. %, 65.0 wt. %, 70.0 wt. %, 75.0 wt. %, 80.0 wt. %, 85.0 wt. %, 90.0 wt. %, 95.0 wt. %, 99.0 wt. %, 99.5 wt. %, or 100.0 wt. %. Ranges expressly disclosed include combinations of any of the above-enumerated upper and lower limits; e.g., 10.0 to 100.0 wt. %, 12.5 to 99.5 wt. %, 20.0 to 90.0, 50.0 to 99.0 wt. %, etc.

As used herein the term "oxygenate", and "oxygenate composition," and the like refer to oxygen-containing compounds having 1 to about 50 carbon atoms, 1 to about 20 carbon atoms, 1 to about 10 carbon atoms, or 1 to about 4 carbon atoms. Exemplary oxygenates include alcohols, ethers, carbonyl compounds, e.g., aldehydes, ketones and carboxylic acids, and mixtures thereof. Particular oxygenates include methanol, ethanol, dimethyl ether, diethyl ether, methylethyl ether, di-isopropyl ether, dimethyl carbonate, dimethyl ketone, formaldehyde, and acetic acid.

In particular embodiments, the oxygenate comprises one or more alcohols, preferably alcohols having 1 to about 20 carbon atoms, 1 to about 10 carbon atoms, or 1 to about 4 carbon atoms. The alcohols useful as first mixtures may be linear or branched, substituted or unsubstituted aliphatic alcohols and their unsaturated counterparts. Non-limiting examples of such alcohols include methanol, ethanol, propanols (e.g., n-propanol, isopropanol), butanols (e.g., n-butanol, sec-butanol, tert-butyl alcohol), pentanols, hexanols, etc. and mixtures thereof. In any embodiment described herein, the first mixture may be one or more of methanol, and/or ethanol, particularly methanol. In any embodiment, the first mixture may be methanol and dimethyl ether.

The oxygenate, particularly where the oxygenate comprises an alcohol (e.g., methanol), may optionally be subjected to dehydration, e.g., catalytic dehydration over γ-alumina. Typically, such catalytic dehydration decreases the amount of water in the oxygenate by converting a portion of the water and alcohol to an ether, e.g., dimethyl ether (DME), in the first mixture. Further optionally, at least a portion of any methanol and/or water remaining in the first mixture after catalytic dehydration may be separated from the first mixture.

In any embodiment, one or more other compounds may be present in the first mixture. Some common or useful such compounds have 1 to about 50 carbon atoms, 1 to about 20 carbon atoms, 1 to about 10 carbon atoms, or 1 to about 4 carbon atoms. Typically, although not necessarily, such compounds include one or more heteroatoms other than oxygen. Some such compounds include amines, halides, mercaptans, sulfides, and the like. Particular such compounds include alkyl-mercaptans (e.g., methyl mercaptan and ethyl mercaptan), alkyl-sulfides (e.g., methyl sulfide), alkyl-amines (e.g., methyl amine), alkyl-halides (e.g., methyl chloride and ethyl chloride). In particular embodiments, the first mixture includes one or more of ≥1.0 wt. % acetylene, pyrolysis oil or aromatics, particularly $C_6$ and/or $C_7$ aromatics. The upper limit on the amount of such other compounds in the first mixture may be 2.0 wt. %, 5.0 wt. %, 10.0 wt. %, 15.0 wt. %, 20.0 wt. %, 25.0 wt. %, 30.0 wt. %, 35.0 wt. %, 40.0 wt. %, 45.0 wt. %, 50.0 wt. %, 60.0 wt. %, 75.0 wt. %, 90.0 wt. %, or 95.0 wt. %. The lower limit on the amount of such other compounds in the first mixture may be 2.0 wt. %, 5.0 wt. %, 10.0 wt. %, 15.0 wt. %, 20.0 wt. %, 25.0 wt. %, 30.0 wt. %, 35.0 wt. %, 40.0 wt. %, 45.0 wt. %, 50.0 wt. %, 60.0 wt. %, 75.0 wt. %, or 90.0 wt. %. Ranges expressly disclosed include combinations of any of the above-enumerated upper and lower limits; e.g., 1.0 to 10.0 wt. %, 2.0 to 5.0 wt. %, 10.0 to 95.0 wt. %, wt. %, 15.0 to 90.0 wt. %, 20.0 to 75.0 wt. %, 25.0 to 60 wt. %, 30.0 to 50 wt. %, 35.0 to 45 wt. %, about 40.0 wt. %, etc.

The catalyst used herein is a composition of matter comprising a molecular sieve and a Group 2-14 element of the Periodic Table. In this sense, the term "comprising" can also mean that the catalyst can comprise the physical or chemical reaction product of the molecular sieve and the Group 2-14 element. Optionally, the catalyst may also include a filler or binder and may be combined with a carrier to form slurry.

For the purposes of this description and claims, reference to a group number for an element corresponds to the current IUPAC numbering scheme for the periodic table. Therefore, a "Group 4 metal" is an element from Group 4 of the Periodic Table, e.g., Hf, Ti, or Zr. The more preferred molecular sieves are SAPO molecular sieves, and metal-substituted SAPO molecular sieves. In particular embodiments, one or more Group 2 elements (e.g., Be, Mg, Ca, Sr, Ba, and Ra) may be used. In other embodiments, one or more Group 3 elements (e.g., Sc and Y), a Lanthanide (e.g., La, Ce, Pr, Nd, Sm, Eu, Gd, Tb, Dy, Ho, Er, Tm, Yb, and Lu), and/or an Actinide may be used. Catalysts comprising at least one Group 4 transition metal (e.g., Ti, Zr, and Hf) may be particularly useful. Likewise, some catalysts may benefit from the presence of at least one Group 5 and/or Group 6 element (e.g., V, Nb, Ta, Cr, Mo, and W). One or more Group 7-9 element (e.g., Mn, Tc, Re, Fe, Ru, Os, Co, Rh, and Ir) may also be used. In some embodiments, the Group 2-14 element comprises one or more Group 11 and/or Group 12 elements (e.g., Cu, Ag, Au, Zn, and Cd) may be used. In still other embodiments, one or more Group 13 elements (B, Al, Ga, In, and Tl). In a preferred embodiment, the metal is selected from the group consisting of Zn, Cd, Ag, and Cu, ideally Zn.

The molecular sieve comprises ≥10.0 wt. % of the catalyst. The upper limit on the amount of molecular sieve in the catalyst may be 10.0 wt. %, 12.5 wt. %, 15.0 wt. %, 20.0 wt. %, 25.0 wt. %, 30.0 wt. %, 35.0 wt. % 40.0 wt. %, 45.0 wt. %, 50.0 wt. %, 55.0 wt. %, 60.0 wt. %, 65.0 wt. %, 70.0 wt. %, 75.0 wt. %, 80.0 wt. %, 85.0 wt. %, 90.0 wt. %, 95.0 wt. %, 99.0 wt. %, 99.5 wt. %, or 100.0 wt. %. The lower limit on the amount of molecular sieve in the catalyst may be 10.0 wt. %, 12.5 wt. %, 15.0 wt. %, 20.0 wt. %, 25.0 wt. %, 30.0 wt. %, 35.0 wt. % 40.0 wt. %, 45.0 wt. %, 50.0 wt. %, 55.0 wt. %, 60.0 wt. %, 65.0 wt. %, 70.0 wt. %, 75.0 wt. %, 80.0 wt. %, 85.0 wt. %, 90.0 wt. %, 95.0 wt. %, 99.0 wt. %, 99.5 wt. %, or 100.0 wt. %. Ranges expressly disclosed include combinations of any of the above-enumerated upper and lower limits; e.g., 10.0 to 20.0 wt. %, 12.5 to 25.0 wt. %, 20.0 to 50.0, or 40.0 to 99.0 wt. %.

As used herein the term "molecular sieve" refers to crystalline or non-crystalline materials having a porous structure. Microporous molecular sieves typically have pores having a diameter of ≤about 2.0 nm. Mesoporous molecular sieves typically have pores with diameters of about 2 to about 50 nm. Macroporous molecular sieves have pore diameters of >50.0 nm. The upper limit on the pore diameter may be $1.00 \times 10^4$ nm, $5.00 \times 10^3$ nm, $2.50 \times 10^3$ nm, $1.00 \times 10^3$ nm, $5.00 \times 10^2$ nm, $2.50 \times 10^2$ nm, $1.25 \times 10^2$ nm, 75.0 nm, 50.0 nm, 40.0 nm, 30.0 nm, 20.0 nm, 10.0 nm, or 5.0 nm. The lower limit on the pore diameter may be $5.00 \times 10^3$ nm, $2.50 \times 10^3$ nm, $1.00 \times 10^3$ nm, $5.00 \times 10^2$ nm, $2.50 \times 10^2$ nm, $1.25 \times 10^2$ nm, 75.0 nm, 50.0 nm, 40.0 nm, 30.0 nm, 20.0 nm, 10.0 nm, 5.0 nm, 4.0 nm, 3.0 nm, 2.0 nm, 1.0 nm or less. Ranges of the pore diameters expressly disclosed include combinations of any of the above-enumerated upper and lower limits. For example, some molecular sieves may have pore diameters of about 1.0 to $>5.00 \times 10^3$ nm, 2.0 to $5.00 \times 10^3$ nm, 2.0 to $1.00 \times 10^3$ nm, 2.0 to $5.00 \times 10^2$ nm, 2.0 to $2.50 \times 10^2$ nm, 2.0 to $1.25 \times 10^2$ nm, 2.0 to 75.0 nm, 5.0 to 75.0 nm, 7.5 to 75.0 nm, 10.0 to 75.0 nm, 15.0 to 75.0 nm, 20.0 to 75.0 nm, 25.0 to 75.0 nm, 2.0 to 50.0 nm, 5.0 to 50.0 nm, 7.5 to 50.0 nm, 10.0 to 50.0 nm, 15.0 to 50.0 nm, 20.0 to 50.0 nm, or 25.0 to 50.0 nm, etc.

Additionally or alternatively, some molecular sieves useful herein are described by a Constraint Index of about 1 to about 12. The upper limit on the range of the Constraint Index may be about 12.0, 11.0, 10.0, 9.0, 8.0, 7.0, 6.0, 5.0, 4.0, 3.0, or 2.0. The lower limit on the range of the Constraint Index may be about 11.0, 10.0, 9.0, 8.0, 7.0, 6.0, 5.0, 4.0, 3.0, 2.0, or 1.0. Ranges of the Constraint Indices expressly disclosed include combinations of any of the above-enumerated upper and lower limits. For example, some molecular sieves have a Constraint Index of 1.0 to about 10.0, 1.0 to about 8.0, 1 to about 6.0, 1 to about 5.0, 1 to about 3.0, 2.0 to about 11.0, 3.0 to 10.0, 4.0 to 9.0, or 6.0 to 9.0, etc. Constraint Index is determined as described in U.S. Pat. No. 4,016,218, incorporated herein by reference for details of the method.

Particular molecular sieves are zeolitic materials. Zeolitic materials are crystalline or para-crystalline materials. Some zeolites are aluminosilicates comprising [$SiO_4$] and [$AlO_4$] units. Other zeolites are aluminophosphates (AlPO) having structures comprising [$AlO_4$] and [$PO_4$] units. Still other zeolites are silicoaluminophosphates (SAPO) comprising [$SiO_4$], [$AlO_4$], and [$PO_4$] units.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18, AlPO-34 and metal containing derivatives thereof, such as one or a combination of SAPO-18, SAPO-34, AlPO-34, AlPO-18, and metal containing derivatives thereof, and especially one or a combination of SAPO-34, AlPO-18, and metal containing derivatives thereof.

Additionally or alternatively, the molecular sieves useful herein may be characterized by a ratio of Si to Al. In particular embodiments, the molecular sieves suitable herein include those having a Si/Al ratio of about 10 to 100, preferably about 10 to 80, more preferably about 20 to 60, and most preferably about 20 to 40.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496, published Apr. 16, 1998, both of which are herein fully incorporated by reference.

Particular molecular sieves useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-34 (U.S. Pat. No. 4,079,095) ZSM-35 (U.S. Pat. No. 4,016,245); ZSM-48 (U.S. Pat. No. 4,397,827); ZSM-57 (U.S. Pat. No. 4,046,685); and ZSM-58 (U.S. Pat. No. 4,417,780). The entire contents of the above references are incorporated by reference herein. Other useful molecular sieves include MCM-22, PSH-3, SSZ-25, MCM-36, MCM-49 or MCM-56, with MCM-22. Still other molecular sieves include Zeolite T, ZKS, erionite, and chabazite.

The catalyst also includes at least one element selected from Groups 2-14 of the Periodic Table. Typically, the total weight of the Group 2-14 elements is ≥0.1 wt. % based on the total weight of the catalyst. Typically, the total weight of the Group 2-14 element is ≤about 10.0 wt. %, based on the total weight of the catalyst. Thus, the upper limit on the range of the amount of the Group 2-14 elements added to the molecular sieve may be 10.0 wt. %, 9.0 wt. %, 8.0 wt. %, 7.0 wt. %, 6.0 wt. %, 5.0 wt. %, 4.0 wt. %, 3.0 wt. %, 2.0 wt. %, 1.0 wt. %, or 0.1 wt. %. The lower limit on the range of the amount of the Group 2-14 elements added to the molecular sieve may be 10.0 wt. %, 9.0 wt. %, 8.0 wt. %, 7.0 wt. %, 6.0 wt. %, 5.0 wt. %, 4.0 wt. %, 3.0 wt. %, 2.0 wt. %, 1.0 wt. %, or 0.1 wt. %. Ranges expressly disclosed include combinations of any of the above-enumerated upper and lower limits; e.g., 0.1 to 10.0 wt. %, 0.1 to 8.0 wt. %, 0.1 to 6.0 wt. %, 0.1 to 5.0 wt. %, 0.1 to 4.0 wt. %, 0.1 to 3.0 wt. %, 0.1 to 2.0 wt. %, 0.1 to 1.0 wt. %, 1.0 to 10.0 wt. %, 1.0 to 9.0 wt. %, 1.0 to 8.0 wt. %, 1.0 to 7.0 wt. %, 1.0 to 6.0 wt. %, 1.0 to 5.0 wt. %, 1.0 to 4.0 wt. %, 1.0 to 3.0 wt. %, etc. Of course, the total weight of the Group 2-14 elements shall not include amounts attributable to the molecular sieve itself.

Particular molecular sieves and Group 2-14-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (El APSO where El is Be, B, Cr, Co, Ga, Fe, Mg, Mn, Ti, or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti, or Zn), U.S. Pat. No. 4,310,440 (AlPO4), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326, and 5,478,787 (MgAPSO), U.S. Pat. No. 4,554,143 (FeAPO), U.S. Pat. Nos. 4,686,092, 4,846,956, and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617, and 4,880,520 (TiAPSO), U.S. Pat. Nos. 4,500,651, 4,551,236, and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066, and 5,675,050, all of which are herein fully incorporated by reference. Other molecular sieves include those described in R. Szostak, Handbook of Molecular Sieves, Van Nostrand Reinhold, New York, N.Y. (1992), which is herein fully incorporated by reference.

In one embodiment, the molecular sieve as modified by the Group 2-14 element is a ZSM-5 based molecular sieve and the Group 2-14, element is selected from elements of Groups 11-12, particularly Zn.

Various methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), International Patent Application WO 01/36329 published May 25, 2001 (surfactant synthesis), International Patent Application WO 01/25151 published Apr. 12, 2001 (staged acid addition), International Patent Application WO 01/60746 published Aug. 23, 2001 (silicon oil), U.S. Patent Application Publication No. 2002-0055433 published May 9, 2002 (cooling molecular sieve), U.S. Pat. No. 6,448,197 (metal impregnation including copper), U.S. Pat. No. 6,521,562 (conductive microfilter), and U.S. Patent Application Publication No. 2002-0115897 published Aug. 22, 2002 (freeze drying the molecular sieve), which are all herein incorporated by reference in their entirety.

Figure 1:
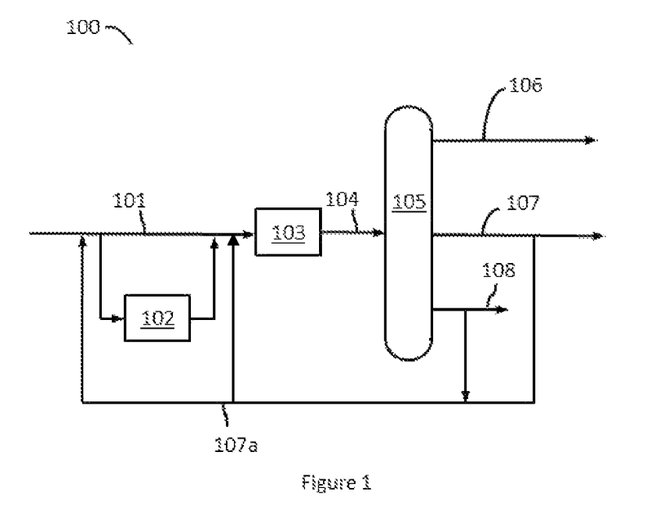
FIG. 1 illustrates a process according to an embodiment of the invention.

A process for converting an oxygenate-containing first mixture to a hydrocarbon stream containing aromatic molecules in the present of the catalyst described above will now be described. FIG. 1 schematically illustrates a process 100 wherein an oxygenated-containing feed is provided via line 101 to a reactor 103 and/or, optionally, to an optional dehydration unit 102 and then or to a reactor 103. Reactor 103 may be any reactor suitable for converting an oxygenate-containing first mixture to an aromatics-containing hydrocarbon effluent. In any embodiment, the reactor 103 may include one or more batch reactor or fixed bed reactor having the catalyst therein, Where reactor 103 includes more than one reactor, the reactors may be arranged in any suitable configuration, e.g., in series, parallel, or series-parallel. Typically, but not necessarily, the reactor 103 is a fixed-bed reactor.

Reactor 103 is operated under conditions to produce a product stream comprising water, one or more hydrocarbons, hydrogen, and one or more oxygenates, wherein said one or more hydrocarbons comprise ≥30.0 wt. % of aromatics, based on the weight of said one or more hydrocarbons in the product stream. In particular embodiments, the amount of aromatics in the hydrocarbon may be 30.0 to 100.0 wt. %, 40.0 to 100.0 wt. %, 50.0 to 100.0 wt. %, 60.0 to 100 wt. %, 70.0 to 100.0 wt. %, 80.0 to 100.0 wt. %, 90.0 to 100.0 wt. %, 95.0 to 100 wt. %; 30.0 to 95.0 wt. %, 40.0 to 95.0 wt. %, 50.0 to 95.0 wt. %, 60.0 to 95 wt. %, 70.0 to 95.0 wt. %, 80.0 to 95.0 wt. %, 90.0 to 95.0 wt. %, 30.0 to 90.0 wt. %, 40.0 to 90.0 wt. %, 50.0 to 90.0 wt. %, 60.0 to 90 wt. %, 70.0 to 90.0 wt. %, 80.0 to 90.0 wt. %, 30.0 to 80.0 wt. %, 40.0 to 80.0 wt. %, 50.0 to 80.0 wt. %, 60.0 to 80 wt. %, 70.0 to 80.0 wt. %, 30.0 to 70.0 wt. %, 40.0 to 70.0 wt. %, 50.0 to 70.0 wt. %, 60.0 to 70 wt. %, 30.0 to 60.0 wt. %, 40.0 to 60.0 wt. %, about 50.0 wt. %, 30.0 to 40.0 wt. %, 30.0 to 50.0 wt. %, or 40.0 to 50.0 wt. %.

In particular embodiments, the aromatics comprise ≥10.0 wt. % paraxylene based on the weight of the aromatics. The upper limit on the amount of para-xylene in the aromatics of the hydrocarbon component of the product stream may be 10.0 wt. %, 20.0 wt. %, 30.0 wt. %, 40.0 wt. %, 45.0 wt. %, 50.0 wt. %, 55.0 wt. %, 60.0 wt. %, 65.0 wt. %, 70.0 wt. %, 80.0 wt. %, 90.0 wt. %, 95.0 wt. %, or 100.0 wt. %. The lower limit of the amount of para-xylene in the aromatics portion of the hydrocarbon of the product stream exiting reactor 103 may be 10.0 wt. %, 20.0 wt. %, 30.0 wt. %, 40.0 wt. %, 45.0 wt. %, 50.0 wt. %, 55.0 wt. %, 60.0 wt. %, 65.0 wt. %, 70.0 wt. %, 80.0 wt. %, 90.0 wt. %, or 95.0 wt. %. Ranges of temperatures expressly disclosed include combinations of any of the above-enumerated upper and lower limits, e.g., 10.0 to 95.0 wt. %, 20.0 to 80.0 wt. %, 30.0 to 70.0 wt. %, 40.0 to 60.0 wt. %, 10.0 to 50.0 wt. %, 20.0 to 60.0 wt. %, or 30.0 to 50.0 wt. %, etc.

In particular embodiments, the hydrocarbons of the product stream comprises ≥80.0 wt. % of aromatics, based on the weight of the hydrocarbon, and ≤30.0 wt. % of the aromatics comprise durene, based on the weight of the aromatics. In particular embodiments, the amount of aromatics in the hydrocarbon of the product stream may be 80.0 to 100.0 wt. %, 85.0 to 100.0 wt. %, 90.0 to 100.0 wt. %, 95.0 to 100.0 wt. %, 80.0 to 95.0 wt. %, 85.0 to 95.0 wt. %, 90.0 to 95.0 wt. %, 80.0 to 90.0 wt. %, or 85.0 to 95.0 wt %; and the amount of durene in the aromatics comprises 0 to 30.0 wt. %, 0 to 25.0 wt. %, 0 to 20.0 wt. %, 0 to 15.0 wt. %, 0 to 10.0 wt. %, 0.0 to 5.0 wt. %, 0 to 2.5 wt. %, 0 to 1.0 wt. %, 1.0 to 30.0 wt. %, 1.0 to 25.0 wt. %, 1.0 to 20.0 wt. %, 1.0 to 15.0 wt. %, 1.0 to 10.0 wt. %, 1.0 to 5.0 wt. %, 1.0 to 2.5 wt. %, 2.5 to 30.0 wt. %, 2.5 to 25.0 wt. %, 2.5 to 20.0 wt. %, 2.5 to 15.0 wt. %, 2.5 to 10.0 wt. %, 2.5 to 5.0 wt. %, 5.0 to 30.0 wt. %, 5.0 to 25.0 wt. %, 5.0 to 20.0 wt. %, 5.0 to 15.0 wt. %, 5.0 to 10.0 wt. %, 10.0 to 30.0 wt. %, 10.0 to 25.0 wt. %, 10.0 to 20.0 wt. %, 10.0 to 15.0 wt. %, 15.0 to 30.0 wt. %, 15.0 to 25.0 wt. %, 15.0 to 20.0 wt. %, 20.0 to 30.0 wt. %, 20.0 to 25.0 wt. %, or 25.0 to 30.0 wt. %.

One of the products in the product stream exiting reactor 103 is hydrogen. Preferably hydrogen is present in an amount ≥0.05 wt. %. The upper limit on the amount of hydrogen in some embodiments is 5.0 wt. %, 4.0 wt. %, 3.0 wt. %, 2.0 wt. %, 1.0 wt. %, 0.50 wt. %, 0.40 wt. %, 0.30 wt. %, 0.20 wt. %, 0.10 wt. %, or 0.05 wt. %. The lower limit on the amount of hydrogen in some embodiments is 5.0 wt. %, 4.0 wt. %, 3.0 wt. %, 2.0 wt. %, 1.0 wt. %, 0.50 wt. %, 0.40 wt. %, 0.30 wt. %, 0.20 wt. %, 0.10 wt. %, or 0.05 wt. %. Ranges of temperatures expressly disclosed include combinations of any of the above-enumerated upper and lower limits, e.g., 0.05 wt. % to about 5.0 wt. %, 0.10 to 4.0 wt. %, 0.2 to 3.0 wt. %, 0.4 to 2.0 wt. %, or 0.5 to 1.0 wt. %.

In particular embodiments, the product stream from reactor 103 comprises ≤1.0 wt. % carbon monoxide, the weight percent of carbon monoxide being based on the total weight of the product stream. Exemplary amounts of carbon monoxide include 0 to 1.0 wt. %, 0 to 0.9 wt. %, 0 to 0.8 wt. %, 0 to 0.7 wt. %, 0 to 0.6 wt. %, 0 to 0.5 wt. %, 0 to 0.4 wt. %, 0 to 0.2 wt. %, 0 to 0.1 wt. %, 0.1 to 0.9 wt. %, 0.1 to 0.8 wt. %, 0.1 to 0.7 wt. %, 0.1 to 0.6 wt. %, 0.1 to 0.5 wt. %, 0.1 to 0.4 wt. %, 0.1 to 0.3 wt. %, 0.1 to 0.2 wt. %, 0.2 to 0.9 wt. %, 0.2 to 0.8 wt. %, 0.2 to 0.7 wt. %, 0.2 to 0.6 wt. %, 0.2 to 0.5 wt. %, 0.2 to 0.4 wt. %, 0.2 to 0.3 wt. %, 0.3 to 0.9 wt. %, 0.3 to 0.8 wt. %, 0.3 to 0.7 wt. %, 0.3 to 0.6 wt. %, 0.3 to 0.5 wt. %, 0.3 to 0.4 wt. %, 0.4 to 0.9 wt. %, 0.4 to 0.8 wt. %, 0.4 to 0.7 wt. %, or 0.4 to 0.6 wt. %. Low carbon monoxide production is desirable in combination with higher hydrogen combinations in some embodiments.

The particularly desirable combination of products in the reactor effluent is provided by selection of reaction conditions for use in combination with the molecular sieve and Group 2-14 element. Thus, in particular embodiments, the reactor 103 is operated at a weight hourly space velocity (WHSV) in the range of from 0.50 to 12.0 hr$^{-1}$. The WHSV may be 0.5 to 11.0 hr$^{-1}$, 0.5 to 10.0 hr$^{-1}$, 0.5 to 9.0 hr$^{-1}$, 0.5 to 7.0 hr$^{-1}$, 0.5 to 6.0 hr$^{-1}$, 0.5 to 5.0 hr$^{-1}$, 0.5 to 4.0 hr$^{-1}$, 0.5 to 3.0 hr$^{-1}$, 0.5 to 2.0 hr$^{-1}$, 0.5 to 1.0 hr$^{-1}$, 1.0 to 11.0 hr$^{-1}$, 1.0 to 10.0 hr$^{-1}$, 1.0 to 9.0 hr$^{-1}$, 1.0 to 7.0 hr$^{-1}$, 1.0 to 6.0 hr$^{-1}$, 1.0 to 5.0 hr$^{-1}$, 1.0 to 4.0 hr$^{-1}$, 1.0 to 3.0 hr$^{-1}$, 1.0 to 2.0 hr$^{-1}$, 2.0 to 11.0 hr$^{-1}$, 2.0 to 10.0 hr$^{-1}$, 2.0 to 9.0 hr$^{-1}$, 2.0 to 7.0 hr$^{-1}$, 2.0 to 6.0 hr$^{-1}$, 2.0 to 5.0 hr$^{-1}$, 2.0 to 4.0 hr$^{-1}$, 2.0 to 3.0 hr$^{-1}$, 3.0 to 11.0 hr$^{-1}$, 3.0 to 10.0 hr$^{-1}$, 3.0 to 9.0 hr$^{-1}$, 3.0 to 7.0 hr$^{-1}$, 3.0 to 6.0 hr$^{-1}$, 3.0 to 5.0 hr$^{-1}$, 3.0 to 4.0 hr$^{-1}$, 4.0 to 11.0 hr$^{-1}$, 4.0 to 10.0 hr$^{-1}$, 4.0 to 9.0 hr$^{-1}$, 4.0 to 7.0 hr$^{-1}$, 4.0 to 6.0 hr$^{-1}$, or about 0.50 hr$^{-1}$.

Additionally or alternatively, the first mixture comprising the oxygenate is exposed in reactor 103 to a temperature ≥400° C. and a pressure ≥2 bar absolute. In particular embodiments, the temperature may be 400.0 to 700.0° C. The upper limit on the range of temperatures may be 400.0° C., 425.0° C., 450.0° C., 475.0° C., 500.0° C., 525.0° C., 550.0° C., 600° C., 650° C., or 700° C. The lower limit on the range of the temperature of reactor 103 may be 400.0° C., 425.0° C., 450.0° C., 475.0° C., 500.0° C., 525.0° C., 550.0° C., 600° C. Ranges of temperatures expressly disclosed include combinations of any of the above-enumerated upper and lower limits. Such temperature ranges may be used in combination with a reactor pressure of 2.0 to 500.0 bar absolute. In particular embodiments, the upper limit on the range of pressures may be 10.0 bar absolute, 50 bar absolute, 75.0 bar absolute, 100.0 bar absolute, 125.0 bar absolute, 150.0 bar absolute, 175.0 bar absolute, 200.0 bar absolute, 250.0 bar absolute, 300.0 bar absolute, 350.0 bar absolute, 400 bar absolute, or 450 bar absolute, and the lower limit may be 2.0 bar absolute, 5.0 bar absolute, 10.0 bar absolute, 50 bar absolute, 75.0 bar absolute, 100.0 bar absolute, 125.0 bar absolute, 150.0 bar absolute, 175.0 bar absolute, 200.0 bar absolute, 250.0 bar absolute, or 300.0 bar absolute. Ranges and combinations of temperatures and pressures expressly disclosed include combinations of any of the above-enumerated upper and lower limits.

The product stream from reactor 103 is provided via a line 104 to first separation unit 105 for separation into (i) at least one water-rich stream 106, (ii) at least one aromatic-rich hydrocarbon stream 107, and (iii) at least one aromatic-depleted hydrocarbon stream 108. First separation unit 105 may be any suitable separation means, e.g., distillation tower, simulated moving-bed separation unit, high pressure separator, low pressure separator, flash drum, etc. Optionally, at least a portion of aromatics-rich hydrocarbon stream 107 may be recycled to reactor 103 via recycle line 107a, e.g., by combination directly or indirectly with the first mixture in line 101. In particular embodiments, wherein ≥50.0 wt. %, 50.0 to 100 wt. %, 60.0 to 95.0 wt. %, 70.0 to 90.0 wt. %, 80.0 to 85.0 wt. %, of the first mixture's aromatics are the recycled aromatics, weight percents being based on the total amount of aromatics in the first mixture.

Optionally, at least a portion of aromatic-depleted hydrocarbon stream 108 exiting first separation unit 105 may be recycled to reactor 103, e.g., by combination, directly or indirectly, with line 101. In another embodiment, oxygenates in aromatics-depleted hydrocarbon stream 108 may be recovered therefrom. At least a portion of the recovered oxygenates may thereafter be provided to reactor 103. Additionally or alternatively, at least one of ethylene, propylene, and butylenes may be recovered from at least a portion of the aromatics-depleted hydrocarbon stream 108.

Figure 2:
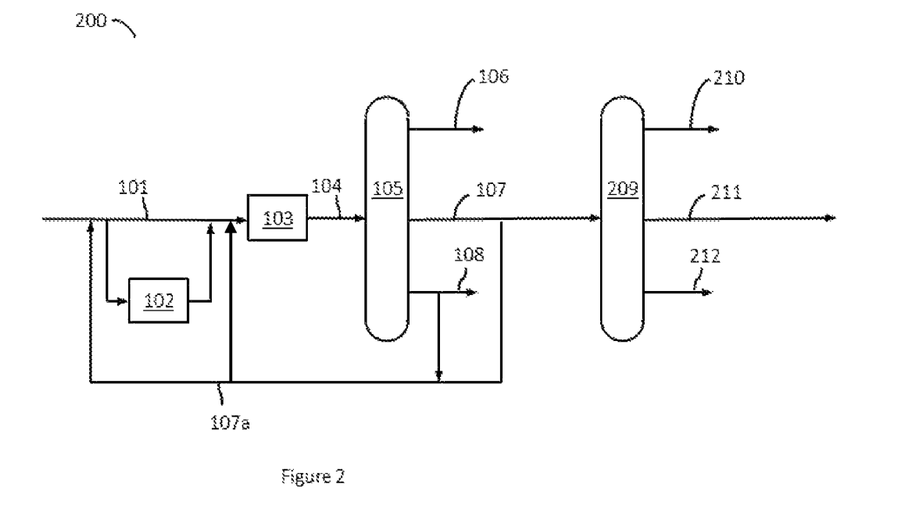
FIG. 2 illustrates a process according to an embodiment of the invention wherein an aromatic-rich hydrocarbon stream is separated into first, second and third streams.

With continuing reference to FIG. 1, FIG. 2 schematically depicts a process 200 according to particular embodiments. The aromatic-rich hydrocarbon stream 107 is provided to a second separation unit 209 configured to separate the aromatic-rich stream into (i) at least one first stream 210 comprising oxygenate and $C_6$ and/or $C_7$ aromatics, (ii) at least one second stream 211 comprising oxygenate and $C_8$ aromatics, and (iii) at least one third stream 212 comprising oxygenate and $C_{9+}$ aromatics. Second separation unit 209 may be any device or process suitable for performing such a separation, e.g. distillation tower, simulated moving-bed separation unit, high pressure separator, low pressure separator, flash drum, etc.

Figure 3:
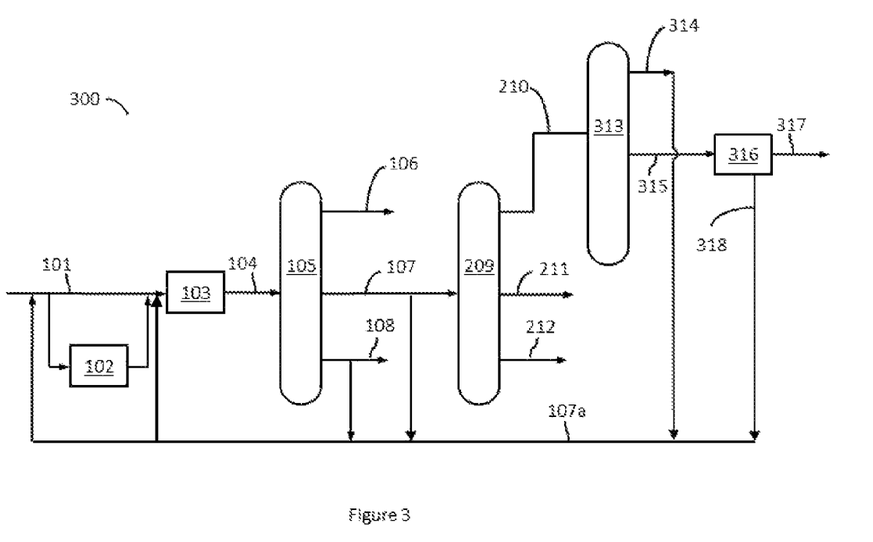
FIG. 3 illustrates a process according to an embodiment of the invention wherein the first stream is separated into a first oxygenate stream and a second aromatics-rich stream comprising $C_6$ and/or $C_7$ aromatics.
Figure 4:
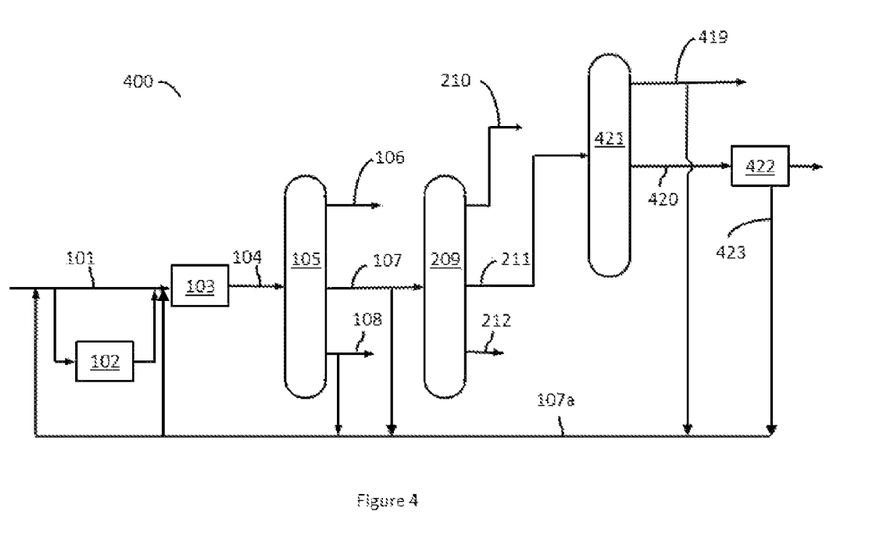
FIG. 4 illustrates a process according to an embodiment of the invention wherein the second stream is separated into a second oxygenate stream and a third aromatics-rich stream.
Figure 5:
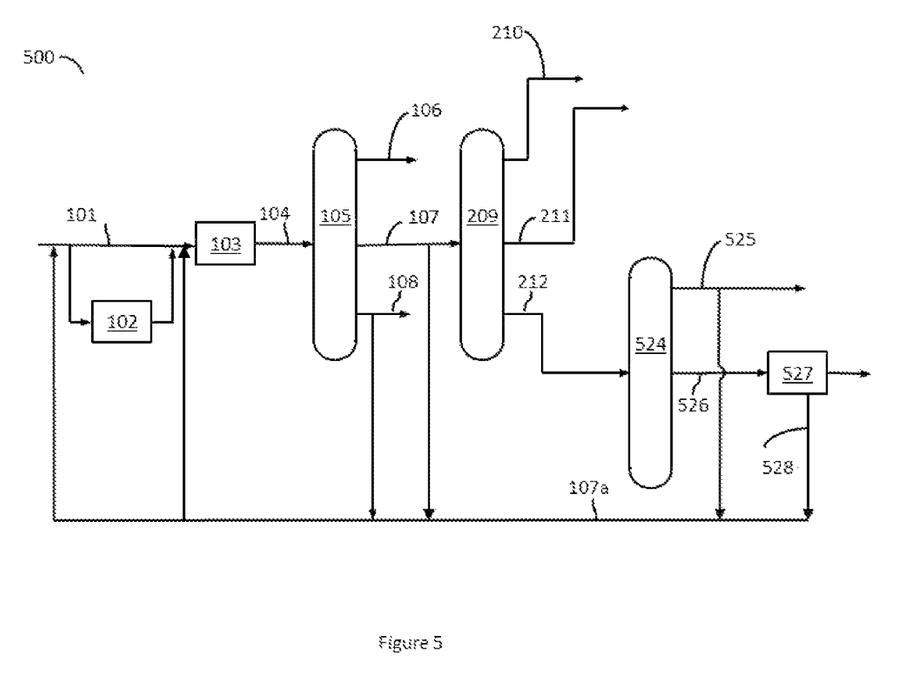
FIG. 5 illustrates a process according to an embodiment of the invention wherein the third stream is separated into a third oxygenate stream and a fourth aromatics-rich stream comprising $C_{9+}$ aromatics.

With continuing reference to FIGS. 1 and 2, FIG. 3 schematically depicts a process 300 according to particular embodiments. Optionally, the first stream 210 may be provided to a third separation unit 313 configured to separate from the first stream 210 a first oxygenate stream 314 and a second aromatics-rich stream 315, the aromatics-rich stream 315 comprising $C_6$ and/or $C_7$ aromatics. Optionally, at least a portion of first oxygenate stream 314 may be recycled to reactor 103, e.g., by combining with the first mixture in line 101, e.g., via line 107a. Third separation unit 313 may be any separation unit suitable for such a separation, e.g., distillation tower, simulated moving-bed separation unit, high pressure separator, low pressure separator, flash drum, etc. In particular embodiments, the second aromatics-rich stream 315 is provided to a recovery unit 316 for recovering benzene and or toluene therefrom via line 317. At least a portion of residual fraction 318 exiting recovery unit 316 may be combined with the first mixture and provided to the reactor 103 via line 101, e.g., via recovery line 107a. Optionally, at least a portion of the second aromatics-rich stream 315, benzene, or toluene 317 is provided to a toluene alkylation, toluene disproportionation or transalkylation unit to produce xylenes (not shown in FIG. 3). Toluene alkylation is described in more detail in, for example, U.S. Pat. Nos. 6,423,879; 6,642,426; 6,388,156; 7,799,962; 8,048,388; 8,399,727; and 8,344,197. Toluene disproportionation is described in more detail in, for example, U.S. Pat. Nos. 5,993,642; 6,039,864; 6,198,013; and 6,486,373. Transalkylation is described in more detail in, for example, U.S. Pat. Nos. 7,553,791; 8,071,828; 8,183,424; and 8,481,443.

With continuing reference to FIGS. 1-3, FIG. 4 schematically depicts a process 400 according to particular embodiments. Such embodiments, which may optionally include the separation scheme of process 300, include separating from the second stream 211 a second oxygenate stream 419 and a third aromatics-rich stream 420 in a fourth separation unit 421. Fourth separation unit 421 may be any device or process suitable for performing such a separation, e.g. distillation tower, simulated moving-bed separation unit, high pressure separator, low pressure separator, flash drum, etc. Optionally, at least a portion of second oxygenate stream 419 may be recycled to reactor 103, e.g., by combining directly or indirectly with the first mixture in line 101, e.g., via recycle line 107a. Typically, the third aromatics-rich stream 420 comprises $C_{8+}$ aromatics. Third aromatics-rich stream 420 may be provided to a second recovery unit 422 for recovering para-xylene therefrom. At least a portion of residual fraction 423 exiting recovery unit 422 may be combined with the first mixture and provided to the reactor 103 via line 101, e.g., via recycle line 107a. Optionally, at least a portion of the para-xylene depleted residual fraction 423 may be sent to a xylenes isomerization unit to produce a mixed xylenes stream from which para-xylene may be recovered.

With continuing reference to FIGS. 1-4, FIG. 5 schematically depicts a process 500 according to particular embodiments. Process 500 may, additionally or alternatively, include separating third stream 212 by any suitable means 524 into a third oxygenate stream 525 and a fourth aromatics-rich stream 526, the fourth aromatics-rich stream comprising $C_{9+}$ aromatics. Optionally, at least a portion may be recycled to reactor 103, e.g., by combining directly or indirectly with the first mixture in line 101, e.g., via recycle line 107a. Fourth aromatics stream 526 may optionally be provided to a transalkylation unit 527 to transalkylate at least a portion of the fourth aromatics-rich stream to produce xylenes. Optionally, at least a portion of third oxygenate stream 525 and/or at least a portion of residual fraction 528 exiting transalkylation unit 527 may be recycled, directly or indirectly, to reactor 103, e.g., by combining with the first mixture in line 101 via recycle line 107a.

It has also been found that recycling and combining at least a portion of the aromatics in the hydrocarbon product with the oxygenate unexpectedly leads to one or more of the following advantages. In particular embodiments, recycling and combining at least a portion of the aromatics in the hydrocarbon product provides an increase in the relative amount of aromatics in the hydrocarbon product. The increase in aromatics may be achieved without a significant increase in the rate of catalyst deactivation and/or without a significant increase in the relative amount of durene in the aromatic portion of the hydrocarbon product. Advantageously and contrary to expectations, recycling and combining with the oxygenate at least a portion of the aromatics in the hydrocarbon product does not suppress methanol conversion to aromatic products. Under particular conditions, recycling of the aromatics can actually provide an overall increase in product aromatics content. Surprisingly, the catalyst may not experience a significant increase in deactivation rate, e.g., from over-reacting the recycled aromatics, even at elevated reaction temperatures (e.g., end of run conditions). And under certain conditions, the relative amount of durene in the aromatic portion of the product may not increase, even though recycling of xylenes to a chemical environment rich in $CH_2$ fragments would be expected to result in alkylation to $C_{9+}$ aromatics. At least a portion of the olefins and paraffins in the hydrocarbon product may be recycled as well, leading to further conversion of the olefins and paraffins to aromatics without causing a significant increase in catalyst deactivation.

The embodiments of the invention are illustrated in the following examples.

Example 1

A first mixture comprising 100 wt % methanol is fed to a fixed bed reactor operated at 450° C. and 15 psig. The reactor is packed with a catalyst comprising a ZSM-5 molecular sieve loaded with 1 wt. % Zn and operated a WHSV of 2 hr-1. In this example, essentially all of the feed is converted into hydrocarbons. The effluent stream from the reactor is separated into an aromatic and non-aromatic stream. The aromatics stream contains benzene, toluene, $C_8$ aromatics, and $C_{9+}$ aromatics which are sent to a nearby aromatics plant for further processing by transalkylation, toluene alkylation, toluene disproportionation, or xylenes isomerization. The non-aromatic stream contains light gases and oxygenates, $C_1$ to $C_5$ olefins and paraffins and a mixture of $C_{5+}$ non-aromatics. This non-aromatic overhead stream from the separator is then sent to an olefins plant for further processing. Table 1 shows the resulting product distribution.

TABLE 1

Reactor product distribution for feed containing 100% methanol

| Product | Wt. % |
| --- | --- |
| $C_1$-$C_4$ paraffins | 16.6 |
| Ethylene | 2.6 |
| Propylenes | 3.0 |
| Butyenes | 1.5 |
| $C_{5+}$ | 3.1 |
| Benzene | 3.2 |
| Toluene | 15.5 |
| $C_8$ Aromatics | 22.0 |
| $C_{9+}$ Aromatics | 22.5 |
| $H_2$ | 0.7 |
| Oxygenates | 9.2 |
| Methanol | 100.0 |

Example 2

A first mixture comprising 100% methanol is fed to the reactor under substantially the same conditions as in Example 1. In this example, however, benzene and toluene in the product stream are recycled back into the reactor. The product distribution, which is shown in Table 2 shows a higher selectivity towards aromatics, particularly the $C_8$ and $C_{9+}$ aromatics.

TABLE 2

Reactor product distribution for methanol feed containing benzene and toluene

| Product (%) | Wt. % |
| --- | --- |
| $C_1$-$C_4$ paraffins | 9.2 |
| Ethylene | 1.2 |
| Propylenes | 1.0 |
| Butylenes | 0.5 |
| $C_{5+}$ | 1.1 |

TABLE 2-continued

Reactor product distribution for methanol feed containing benzene and toluene

| Product (%) | Wt. % |
|---|---|
| Benzene | 3.1 |
| Toluene | 16.9 |
| $C_8$ Aromatics | 33.1 |
| $C_{9+}$ Aromatics | 29.5 |
| $H_2$ | 1.7 |
| Oxygenates | 2.6 |
| Methanol Conversion | 100% |
| Benzene Conversion | 55.5% |
| Toluene Conversion | 54.5% |

Example 3

In this example, a first mixture comprising methanol may be provided to a fixed bed reactor which is operated at 400° C. and 1 atm. The reactor is packed with a catalyst comprising a ZSM-5 molecular sieve loaded with 1 wt. % Zn and having a Si:Al ratio of 100 to 10,000 and operated a WHSV of 6 hr$^{-1}$. The product stream comprises 17.2 wt. % $C_6$-$C_9$ aromatic compounds.

Example 4

Example 3 is substantially repeated, except that the reactor temperature is 500° C. The product stream comprises 19.4 wt. %, $C_6$-$C_9$ aromatic compounds.

The description and examples above support one or more of the following more specific Embodiments.

Embodiment 1

An aromatic production process, comprising (a) providing a first mixture comprising ≥10.0 wt. % of at least one oxygenate, based on the weight of the first mixture; (b) contacting said first mixture with a catalyst to convert said first mixture to a product stream comprising water, one or more hydrocarbons, hydrogen, and one or more oxygenates, wherein A) said catalyst comprises at least one molecular sieve and at least one element selected from Groups 2-14 of the Periodic Table; B) said one or more hydrocarbons comprise ≥30.0 wt. % of aromatics, based on the weight of said one or more hydrocarbons in the product stream; and C) separating from said product stream (i) at least one water-rich stream, (ii) at least one aromatic-rich hydrocarbon stream, and (iii) at least one aromatic-depleted hydrocarbon stream.

Embodiment 2

A process according to Embodiment 1, wherein the first mixture comprises ≥90.0 wt. % of methanol and/or DME, and wherein the process further comprises separating from the aromatic-rich hydrocarbon stream (i) at least one first stream comprising oxygenate and $C_6$ and/or $C_7$ aromatics, (ii) at least one second stream comprising oxygenate and $C_8$ aromatics, and (iii) at least one third stream comprising oxygenate and $C_{9+}$ aromatics.

Embodiment 3

A process according to any embodiment encompassed by Embodiment 2, further comprising contacting at least a portion of the first stream with the catalyst in step (b).

Embodiment 4

A process according to any embodiment encompassed by Embodiment 2, further comprising separating from the first stream a first oxygenate stream and a second aromatics-rich stream, the aromatics-rich stream comprising $C_6$ and/or $C_7$ aromatics.

Embodiment 5

A process according to any embodiment encompassed by Embodiment 4, further comprising recovering benzene and/or toluene from the second aromatics-rich stream.

Embodiment 6

A process according to any embodiment encompassed by Embodiments 4 or 5, further comprising sending at least a portion of the second aromatics-rich stream or benzene and/or toluene to a toluene alkylation, toluene disproportionation, or transalkylation unit to produce xylenes.

Embodiment 7

A process according to any embodiment encompassed by Embodiment 2, further comprising separating from the second stream a second oxygenate stream and a third aromatics-rich stream, the third aromatics rich stream comprising $C_{8+}$ aromatics.

Embodiment 8

A process according to any embodiment encompassed by Embodiment 7, further comprising recovering para-xylene and a para-xylene depleted stream from the third aromatics-rich stream.

Embodiment 9

A process according to any embodiment encompassed by Embodiment 8, further comprising sending at least a portion of para-xylene depleted stream to a xylenes isomerization unit to produce a mixed xylenes stream and recovering para-xylene from the mixed xylenes stream.

Embodiment 10

A process according to any embodiment encompassed by Embodiment 2, further comprising separating from the third stream a third oxygenate stream and a fourth aromatics-rich stream, the fourth aromatics-rich stream comprising $C_{9+}$ aromatics.

Embodiment 11

A process according to any embodiment encompassed by Embodiment 10, further comprising transalkylating at least a portion of the fourth aromatics-rich stream to produce xylenes.

Embodiment 12

A process according any embodiment encompassed by any of Embodiments 4, 7, or 10, further comprising contacting at least a portion of the first, the second, or the third oxygenate streams with the catalyst in step (b).

Embodiment 13

A process according to any of Embodiments 1-12, further comprising contacting at least a portion of the aromatic-depleted hydrocarbon stream with the catalyst in step (b).

Embodiment 14

A process according to any of Embodiments 1-13, further comprising recovering oxygenates from the aromatic-depleted hydrocarbon stream.

Embodiment 15

A process according to any embodiment encompassed by Embodiment 14, comprising contacting the catalyst in step (b) with at least a portion of the recovered oxygenates.

Embodiment 16

A process according to any embodiment encompassed by Embodiment 14 or 15, further comprising recovering at least one of ethylene, propylene, and butylene from at least a portion of the aromatic-depleted hydrocarbon stream.

Embodiment 17

An oxygenate conversion process, the process comprising: (a) providing a first mixture, the first mixture comprising ≥10.0 wt. % oxygenate based on the weight of the first mixture; (b) exposing the first mixture at a temperature ≥400° C. at a pressure ≥2 bar absolute in the presence of a catalyst to convert ≥90.0 wt. % of the first mixture's oxygenate to (i) water, (ii) hydrocarbon, and (iii) ≤1.0 wt. % carbon monoxide, the weight percents being based on the weight of oxygenate in the first mixture, wherein (A) the catalyst comprises ≥10.0 wt. % of at least one molecular sieve and ≥0.1 wt. % of at least one element selected from Groups 2-14 of the Periodic Table, the weight percents being based on the weight of the catalyst, (B) the hydrocarbon comprises ≥50.0 wt. % of aromatics, based on the weight of the hydrocarbon; and (C) separating the aromatics from one or more of (i) at least a portion of the water produced in step (b), (ii) any unreacted oxygenate, or (iii) at least a portion of the hydrocarbon.

Embodiment 18

A process according to any embodiment, wherein (i) the first mixture comprises ≥25.0 wt. % oxygenate, based on the weight of the first mixture, and (ii) the oxygenate comprises ≥90.0 wt. % based on the weight of the oxygenate of one or more of alcohol, ether, carboxylic acid, carbon monoxide, or carbon dioxide.

Embodiment 19

A process according to any embodiment, wherein the oxygenate comprises ≥99.0 wt. % of methanol and/or dimethylether.

Embodiment 20

A process according to any embodiment encompassed by Embodiments 17-19, wherein the oxygenate comprises ≥99.0 wt. % of methanol, the exposing of step (b) is conducted at a WHSV in the range of from 0.5 to 12 hr$^{-1}$, the hydrocarbon comprises ≥80.0 wt. % of aromatics, based on the weight of the hydrocarbon, and ≤30.0 wt. % of the aromatics comprise durene, based on the weight of the aromatics.

Embodiment 21

A process according to any embodiment, wherein the first mixture further comprises ≥10.0 wt. % aromatics, based on the weight of the first mixture.

Embodiment 22

A process according to any embodiment encompassed by Embodiments 17-21, further comprising recycling at least a portion of the separated aromatics from step (c) to step (a), wherein ≥50.0 wt. % of the first mixture's aromatics are the recycled aromatics.

Embodiment 23

The process of any embodiment, wherein the molecular sieve comprises ZSM-5, and the Group 2-14 element comprises Zn.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the enforceable scope of the present invention.

All documents described herein are incorporated by reference for purposes of all jurisdictions where such practice is allowed, including any priority documents and/or testing procedures to the extent they are not inconsistent with this text, provided however, that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. An aromatic production process, comprising:
   (a) providing a first mixture comprising ≥10.0 wt. % of at least one oxygenate, based on the weight of the first mixture;
   (b) contacting the first mixture with a catalyst to convert the first mixture to a product stream comprising water, one or more hydrocarbons, hydrogen, and one or more oxygenates, wherein:
      (1) the catalyst comprises at least one molecular sieve and at least one element selected from Groups 2-14 of the Periodic Table; and
      (2) the one or more hydrocarbons comprise ≥30.0 wt. % of aromatics, based on the weight of the one or more hydrocarbons in the product stream;

(c) separating from the product stream (i) a water-rich stream, (ii) an aromatic-rich hydrocarbon stream, and (iii) an aromatic-depleted hydrocarbon stream;
(d) separating from the aromatic-rich hydrocarbon stream (i) a first stream comprising $C_6$ and/or $C_7$ aromatics, (ii) a second stream comprising $C_8$ aromatics, and (iii) a third stream comprising $C_{9+}$ aromatics; and
(e) separating an oxygenate stream from at least one of the first stream, the second stream, or the third stream.

2. The process of claim 1, wherein the first mixture comprises ≥90.0 wt. % of methanol and/or dimethylether.

3. The process of claim 2, further comprising contacting at least a portion of the first stream with the catalyst in step (b).

4. The process of claim 2, wherein the separating in (e) comprises separating from the first stream a first oxygenate stream and a second aromatics-rich stream, the second aromatics-rich stream comprising $C_6$ and/or $C_7$ aromatics.

5. The process of claim 4, further comprising recovering benzene and/or toluene from the second aromatics-rich stream.

6. The process of claim 4, further comprising sending at least a portion of the second aromatics-rich stream to a toluene alkylation, toluene disproportionation or transalkylation unit to produce xylenes.

7. The process of claim 4, further comprising contacting at least a portion of the first oxygenate stream with the catalyst in step (b).

8. The process of claim 2, wherein the separating in (e) comprises separating from the second stream a second oxygenate stream and a third aromatics-rich stream, the third aromatics-rich stream comprising $C_{8+}$ aromatics.

9. The process of claim 8, further comprising recovering para-xylene and a para-xylene depleted stream from the third aromatics-rich stream.

10. The process of claim 9, further comprising sending at least a portion of the para-xylene depleted stream to a xylenes isomerization unit to produce a mixed xylenes stream and recovering para-xylene from the mixed xylenes stream.

11. The process of claim 8, further comprising contacting at least a portion of the second oxygenate stream with the catalyst in step (b).

12. The process of claim 2, wherein the separating in (e) comprises separating from the third stream a third oxygenate stream and a fourth aromatics-rich stream, the fourth aromatics-rich stream comprising $C_{9+}$ aromatics.

13. The process of claim 12, further comprising transalkylating at least a portion of the fourth aromatics-rich stream to produce xylenes.

14. The process of claim 12, further comprising contacting at least a portion of the third oxygenate stream with the catalyst in step (b).

15. The process of claim 1, further comprising contacting at least a portion of the aromatic-depleted hydrocarbon stream with the catalyst in step (b).

16. The process of claim 1, further comprising recovering oxygenates from the aromatic-depleted hydrocarbon stream.

17. The process of claim 16, comprising contacting the catalyst in step (b) with at least a portion of the recovered oxygenates.

18. The process of claim 16, further comprising recovering at least one of ethylene, propylene, and butylenes from at least a portion of the aromatic-depleted hydrocarbon stream.

19. The process of claim 1, wherein the molecular sieve comprises ZSM-5, and the element comprises Zn.

20. An oxygenate conversion process, the process comprising:
(a) providing a first mixture, the first mixture comprising ≥10.0 wt. % oxygenate based on the weight of the first mixture;
(b) contacting the first mixture with a catalyst at a temperature ≥400° C. and a pressure ≥2 bar absolute to convert ≥90.0 wt. % of the first mixture's oxygenate to (i) water, (ii) hydrocarbon, and (iii) ≤1.0 wt. % carbon monoxide, the weight percents being based on the weight of oxygenate in the first mixture, wherein:
(1) the catalyst comprises ≥10.0 wt. % of at least one molecular sieve and ≥0.1 wt. % of at least one element selected from Groups 2-14 of the Periodic Table, the weight percents being based on the weight of the catalyst; and
(2) the hydrocarbon comprises ≥50.0 wt. % of aromatics, based on the weight of the hydrocarbon;
(c) separating from the hydrocarbon (i) an aromatic-rich hydrocarbon stream, and (ii) an aromatic-depleted hydrocarbon stream;
(d) separating from the aromatic-rich hydrocarbon stream (i) a first stream comprising $C_6$ and/or $C_7$ aromatics, (ii) a second stream comprising $C_8$ aromatics, and (iii) a third stream comprising $C_{9+}$ aromatics; and
(e) separating an oxygenate stream from at least one of the first stream, the second stream, or the third stream.

21. The process of claim 20, wherein (i) the first mixture comprises ≥25.0 wt. % oxygenate, based on the weight of the first mixture, and (ii) the oxygenate in the first mixture comprises ≥90.0 wt. % based on the weight of the oxygenate of one or more of alcohol, ether, carboxylic acid, carbon monoxide, or carbon dioxide.

22. The process of claim 21, wherein the oxygenate in the first mixture comprises ≥99.0 wt. % of methanol and/or dimethylether.

23. The process of claim 22, wherein the oxygenate in the first mixture comprises ≥99.0 wt. % of methanol, the contacting of step (b) is conducted at a weight hourly space velocity in the range of from 0.5 to 12 hr$^{-1}$, the hydrocarbon comprises ≥80.0 wt. % of aromatics, based on the weight of the hydrocarbon, and ≤30.0 wt. % of the aromatics comprise durene, based on the weight of the aromatics.

24. The process of claim 20, wherein the first mixture further comprises ≥10.0 wt. % aromatics, based on the weight of the first mixture.

25. The process of claim 20, further comprising recycling at least a portion of aromatics in the aromatic-rich hydrocarbon stream to step (a), wherein ≥50.0 wt. % of the first mixture's aromatics are recycled from the aromatic-rich hydrocarbon stream.

26. The process of claim 20, wherein the molecular sieve comprises ZSM-5, and the element comprises Zn.

* * * * *